United States Patent [19]
Wells et al.

[11] Patent Number: 5,846,191
[45] Date of Patent: Dec. 8, 1998

[54] REDO STERNOTOMY RETRACTOR

[75] Inventors: B. Keith Wells, Marietta; William R. Mayfield, Atlanta, both of Ga.; Gregory R. Furnish, Louisville, Ky.

[73] Assignee: Genzyme Corporation, Framingham, Mass.

[21] Appl. No.: 929,548

[22] Filed: Sep. 15, 1997

Related U.S. Application Data

[63] Continuation-in-part of Ser. No. 713,924, Sep. 13, 1996.
[51] Int. Cl.$^6$ ........................................................ A61B 1/22
[52] U.S. Cl. ........................ 600/201; 600/210; 600/213; 600/215; 600/233; 600/234
[58] Field of Search ..................... 600/201, 204, 600/205, 210, 213, 215, 226, 231, 233, 234, 235

[56] References Cited

U.S. PATENT DOCUMENTS

| | | | |
|---|---|---|---|
| 2,670,732 | 8/1954 | Nelson | 128/20 |
| 3,030,948 | 4/1962 | Loeffler | 128/17 |
| 3,196,865 | 7/1965 | Rose | 128/20 |
| 3,221,743 | 12/1965 | Thompson et al. | 128/303 |
| 3,467,079 | 9/1969 | James | 128/20 |
| 4,050,464 | 9/1977 | Hall | 128/303 |
| 4,151,838 | 5/1979 | Crew | 128/20 |
| 4,323,057 | 4/1982 | Jamieson | 128/17 |
| 5,512,037 | 4/1996 | Russell et al. | 600/206 |
| 5,514,076 | 5/1996 | Ley | 600/206 |
| 5,514,077 | 5/1996 | Rabban | 600/226 |
| 5,554,101 | 9/1996 | Matula et al. | 600/214 |
| 5,588,951 | 12/1996 | Zhu et al. | 600/207 |

*Primary Examiner*—Beverly M. Flanagan
*Attorney, Agent, or Firm*—Neddle & Rosenberg, P.C.

[57] ABSTRACT

A hand-held retractor that is adapted for endoscopic use at a predetermined area of a patient. The retractor is comprised of a longitudinally-extending blade with a proximal end, a distal end, and a top surface. A handle is connected to the proximal end of the blade by a separating member, which is preferably arcuate. The separating member is configured to allow a surgeon direct access to and visualization of the area adjacent the top surface and distal end of the blade after positioning the distal end of the blade at the predetermined area. Also provided is a method of endoscopic retrosternal adhesiolysis which utilizes a retractor to provide access to and visualization of adhesions adjacent the cranial portion of a patient's sternum while retracting away and protecting underlying tissue.

18 Claims, 2 Drawing Sheets

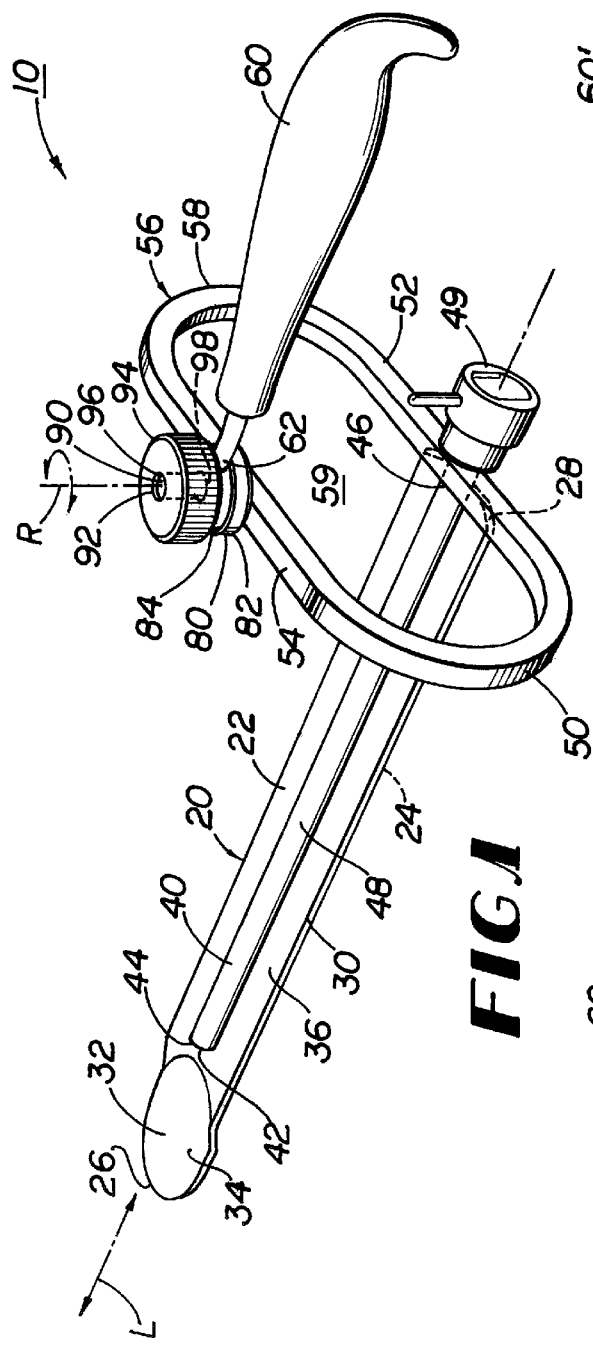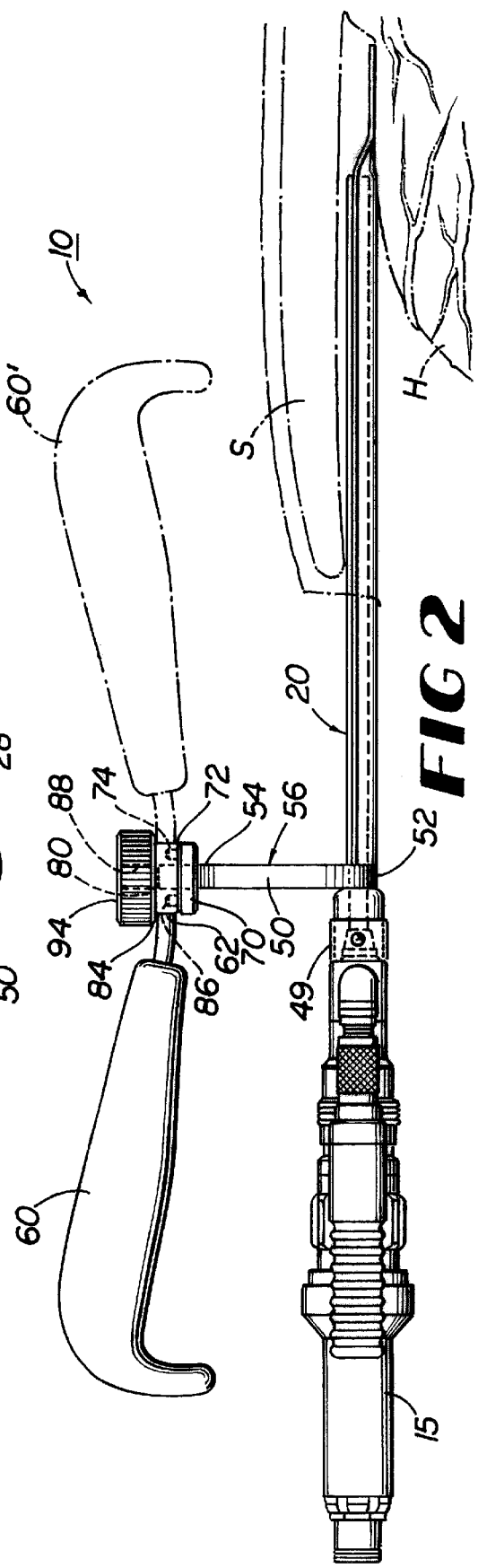

REDO STERNOTOMY RETRACTOR

This application is a continuation-in-part of U.S. Ser. No. 08/713,924, filed Sep. 13, 1996, which is pending.

FIELD OF THE INVENTION

The present invention relates to surgical retractors, and in particular, retractors adapted for endoscopic use. More particularly, the invention relates to a retractor for use in retrosternal adhesiolysis.

BACKGROUND OF THE INVENTION

An anterior (or ventral) midline sternotomy is the most common surgical approach for coronary artery bypass or valvular repair surgery. Approximately 15% of the coronary artery bypass surgery preformed is a second or third surgery to "redo" or repair a previous bypass or add additional bypass grafts. Likewise, approximately 10% of all valvular surgery is redo surgery. Combined, these figures represent nearly 50,000 redo surgeries per year of in the United States alone.

A significant post operative complication of the sternotomy approach is development of retrosternal adhesions between the patient's heart and/or pericardial sac and the anterior chest wall at the incision site. In the event additional coronary surgery becomes necessary, retrosternal adhesions significantly increase the risk of the second or redo sternotomy.

Complications associated with retrosternal adhesions and the redo sternotomy include laceration of the right ventricle that often adheres to the old sternal incision, laceration of the mammary artery or vein graft, laceration of the aorta, laceration of the innominate vein, or a traction tear of right ventricle after sternotomy when raising the sternal table.

Surgeons have developed methods of redo sternotomy to decrease the above risks. Such methods include the use of a cardiopulmonary bypass to decompress the heart in conjunction with the use of an oscillating orthopedic saw or Hall-type saw, and the ART procedure which attempts a takedown of retrosternal adhesions under direct visualization using extreme elevation and retraction of the anterior chest wall.

Unfortunately, the above methods have not been entirely successful at eliminating the risks associated with retrosternal adhesions. In particular, direct visualization and lysis of adhesions near the cranial end of the sternum is difficult because of anatomical constraints. Likewise, decompression may not be completely effective in separating vital structures that become securely adhered to the initial sternotomy incision.

Endoscopic visualization of cranially located retrosternal adhesions offers a viable alternative for reducing the risks associated with redo sternotomy. Endoscopic visualization, when successfully achieved, allows pre-sternotomy right ventricular dissection away from the sternal incision, avoids the necessity of cardiopulmonary bypass, and eliminates the risk of traction injury of the right ventricle when the sternal table is elevated.

Endoscopic visualization, however, has proven to be difficult because of insufficient suitable working space due to impingement of surrounding tissues. This problem is pronounced in obese patients. Accordingly, a need exists for a retractor that can be used in conjunction with an endoscope that prevents impingement of surrounding tissues by creating a dissecting plane between the posterior or dorsal surface of the sternum and underlying tissue.

OBJECTS OF THE INVENTION

It is an object of the present invention to provide a hand-held retractor that is adapted for endoscopic use at a predetermined area of a patient which allows a surgeon access to and visualization of the predetermined area while protecting adjacent structures.

In particular, it is an object of the present invention to provide a retractor that is adapted for endoscopic use which has a low-profile design to facilitate work between the sternum and the heart prior to performing a redo sternotomy procedure.

It is also an object of the invention to provide a method of endoscopic lysis of a retrosternal adhesion at a predetermined area in which visualization is augmented by retraction of tissue at the predetermined site.

It is further an object of the invention to provide a retractor adapted for endoscopic use that is capable of providing direct access to and visualization of the area adjacent the cranial portion of the patient's sternum.

SUMMARY OF THE INVENTION

The present invention provides a hand-held retractor that is adapted for endoscopic use at a predetermined area of a patient. The retractor comprises a longitudinally-extending blunt blade with a proximal end, a distal end, and a top surface. A handle is connected to the proximal end of the blade by a separating member. The separating member is configured to allow a surgeon direct access to and visualization of the area adjacent the top surface and distal end of the blade after positioning the distal end of the blade at the predetermined area. The separating member preferably is arcuate so that the handle is disposed over the blade when the blade is horizontally disposed. For example, the separating member may be either a half arc or a full oval.

BRIEF DESCRIPTION OF THE FIGURES OF THE DRAWINGS

FIG. 1 is a rear perspective view of one embodiment of the retractor of the present invention.

FIG. 2 is a side cross-sectional view of the retractor of FIG. 1 being used with a surgical instrument and showing in phantom line the handle in an alternate position.

DETAILED DESCRIPTION OF THE INVENTION

Figure 3:
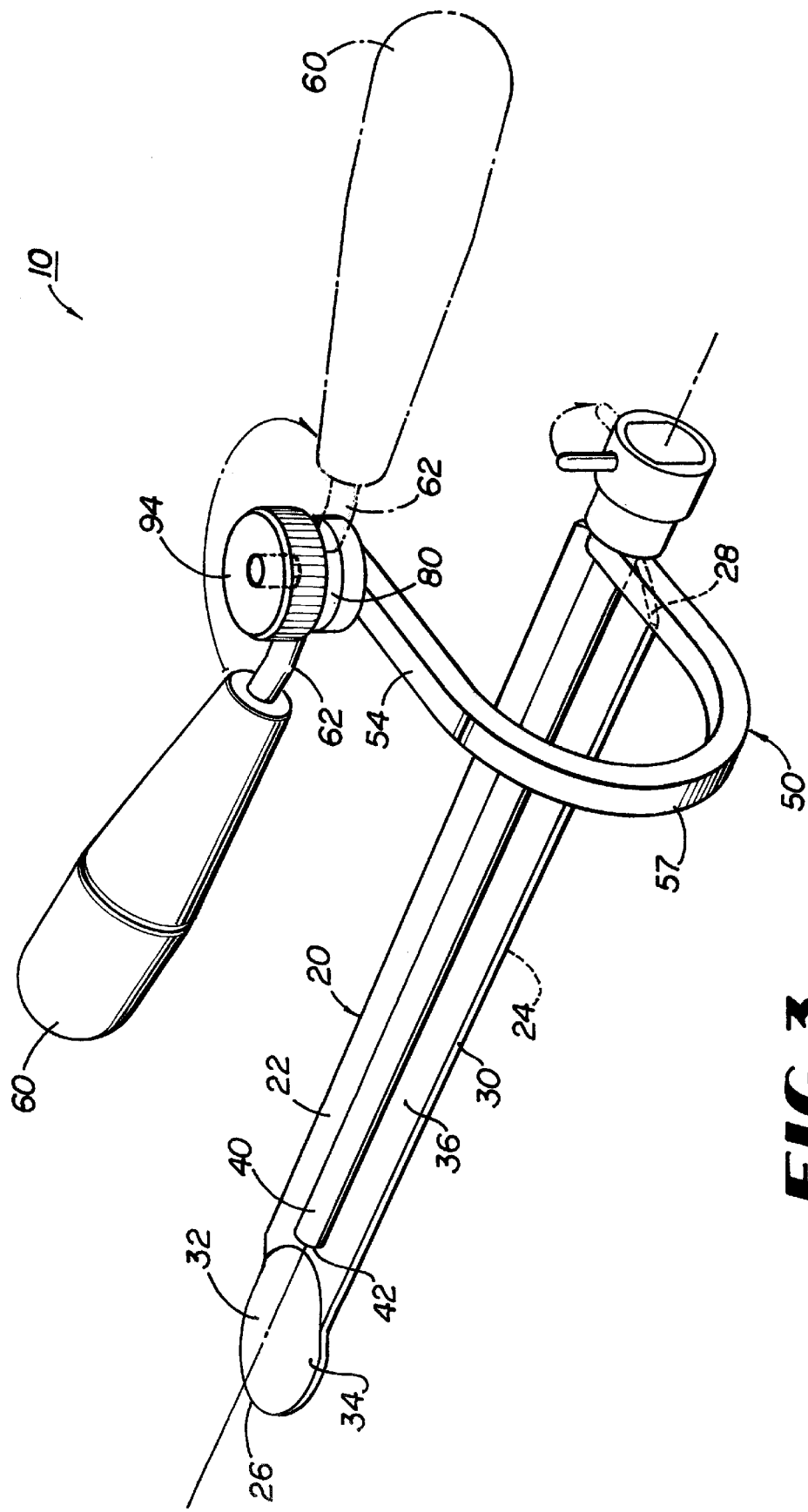
FIG. 3 is a rear perspective view showing an alternative embodiment of the present invention in which the separating member is "C" shaped.

The present invention is more particularly described in the following examples which are intended as illustrative only since numerous modifications and variations therein will be apparent to those skilled in the art. As used in the specification and in the claims, "a" can mean one or more, depending upon the context in which it is used.

Referring to FIGS. 1–3, the present invention comprises a retractor 10, preferably a redo sternotomy retractor, having a longitudinally-extending blunt blade 20, a separating member 50, a handle 60, and a means for connecting the handle 60 to the separating member 50. A preferred use of the retractor 10 is the dissection of and lysis of retrosternal adhesions, e.g., adhesions between the sternum S and heart H or pericardium at a previous sternotomy site. The retractor 10 can be used for other surgical procedures, such as lysis of abdominal adhesions, intrauterine adhesions or other thoracic adhesions and the like, particularly for procedures using endoscopic visualization.

The blunt blade 20 has a longitudinal axis L, a top surface 22, a bottom surface 24, a distal end 26, an opposed proximal end 28, and an edge 30 circumscribing it. The preferred material to construct the retractor 10 is a stainless steel or a biocompatable metal or alloy that is acceptable for surgery. However, other materials are also contemplated, such as plastic.

Referring now to FIG. 2, the preferred length of the blunt blade 20 is about the same as the length of the sternum S of the patient on whom the surgical procedure will be performed, which is approximately ten (10) to twelve (12) inches for an adult patient. For a pediatric operation, the length of the blunt blade 20 would naturally be shorter, such as between about four (4) to six (6) inches.

As shown in FIGS. 1–3, at least a portion of the blunt blade 20 is arcuate in cross section. This is preferred because a curved cross section is stronger and more stable than a flat profile. However, a blunt blade 20 that is substantially rectangular in cross section is contemplated as an alternate embodiment. As one skilled in the art will appreciate, the shape and dimensions of the blunt blade 20, such as length, width, and thickness, can be designed for different, specific surgical procedures. Design factors include the procedure being performed, the structural strength necessary for the blunt blade 20, the desired flexibility of the blunt blade 20, and the predetermined area of the patient's body where the operation will occur. For example, as shown in FIG. 2, an appropriate thickness of the blunt blade 20 is required to ensure a proper operation wherein the distance between the sternum S and the heart H in an adult patient is approximately three (3) to five (5) millimeters.

It is also preferred that at least a portion of the edge 30 of the blunt blade 20 adjacent its distal end 26, or front tip 32, is arcuate. As FIGS. 1 and 3 show, the edge 30 of the front tip 32 has a constant curvature. An alternate embodiment has less angularity, such as a front tip 32 having a squared "C" shape. The edge 30 of the front tip 32 itself should be smooth and blunt, as opposed to having sharp corners, to reduce the chances of tissue damage or other injuries when used during the surgical procedure. The blunt blade 20 repels tissue away from the area of adhesiolysis and protects such tissue from trauma due to electrocautery or sharp dissecting instruments such a scissors or a scalpel.

Another preference for the design of the blunt blade 20 is that the top surface 22 of the section adjacent the front tip 32 is at a lower position than, or drops relative to, the top surface 22 of the rest of the blunt blade 20. The blunt blade 20 comprises a first section 34 disposed adjacent the distal end 26 of the blunt blade 20 and an adjacent second section 36, which is shown as encompassing the remainder of the length of the blunt blade 20. The top surface 22 of the first section 34 and the second section 36 are linear as the respective top surface extends along the longitudinal axis L of the blunt blade 20. At the point where the two sections 34, 36 meet, the top surface 22 is nonlinear. Accordingly, the top surfaces 22 of the first and second sections 34, 36 are nonlinear with respect to each other and, preferably, the top surface 22 of the first section 34 is lower than the top surface 22 of the second section 36. That is, the top surface 22 of the first section 34 is disposed closer to the bottom surface 24 of the first section 34 than the top surface 22 of the second section 36. This design in which the top surface 22 of the section adjacent the front tip 32 is lower is advantageous for use with an endoscopic scope to prevent obstruction of the scope.

As shown in FIGS. 1 and 3, the retractor 10 is preferably designed for endoscopic use and further comprises a longitudinally-extending tube 40 defining a bore 42 therethrough. The tube 40 has a first end 46 disposed adjacent the proximal end 28 of the blunt blade 20, an opposed second end 44 and an outer surface 48. At least a portion of the outer surface 48 is fixedly attached, such as by a weld, to the top surface 22 of the blunt blade 20. The bore 42 extends substantially parallel to the longitudinal axis L of the blunt blade 20 and is of a size to allow a predetermined surgical instrument 15 to be slidably received therein. An example of a surgical instrument is an endoscope. The tube 40 securably and stationarily positions the surgical instrument 15 relative to the blunt blade 20 as the retractor 10 is used.

The diameter of the bore 42 is of an appropriate dimension to accommodate a particular endoscope or surgical instrument 15, such as four (4) or five (5) millimeters for standard endoscopic procedures, or two (2) or three (3) millimeters for pediatric surgery. It is also preferred that the retractor 10 further comprises a bayonet-type endoscopic fitting 49 fixedly attached to the first end 46 of the tube 40. The fitting may detachably secure a predetermined surgical instrument 15 (such as an endoscope) slidably received in the tube 40 at a desired longitudinal position. Other securing devices known in the art can similarly be used.

The separating member 50 of the present invention has a bottom end 52, which is fixedly attached to the proximal end 28 of the blunt blade 20, and an opposed top end 54. The separating member 50 is oriented to allow longitudinal movement of a surgical instrument 15 along at least a portion of the top surface 22 of the blunt blade 20 so that the movement is unobstructed by the separating member 50. That is, the separating member 50 laterally spaces apart the handle 60 from the blunt blade 20 so that a surgical instrument 15 can be passed along the length of the blunt blade 20 without contacting the handle 60 or the separating member 50.

Referring again to FIG. 1, the separating member 50 comprises a ring member 56 having a body portion 58 defining an opening 59 therethrough. The opening 59, which is circular, specifically an oval, is of a size to allow a surgical instrument 15 to be disposed therethrough unobstructed by the body portion 58. The ring member 56 can have other shapes, such as a rectangular opening. It is also contemplated that the opening 59 can be small, such as the same as the bore of the tube 40 and longitudinally-aligned with the tube 40.

FIG. 3 shows another embodiment of the separating member 50, which is a "C" shaped member 57. The "C" shaped member 57, similar to the ring member 56, is at least partially arcuate so that the handle 60 is disposed over the blunt blade 20 when the blade 29 is horizontally disposed. As with the ring member, the "C" shaped member 57 has a bottom end 52 fixedly attached to the proximal end 28 of the blunt blade 20 and an opposed top end 54, to which the handle 60 is attached.

Other designs of separating members 50 that laterally space apart the handle 60 from the blunt blade 20 are also contemplated. One example is a substantially linear member, instead of one with an opening therethrough, that is disposed laterally and substantially parallel to the top surface 22 of the blunt blade 20. Thus, the handle 60 would be located to the side of the blunt blade 20 so that the handle 60 would be aligned sideways instead of over the top surface 22 of the blunt blade 20, as shown in FIGS. 1–3. A purpose of a separating member used with the present invention is to remove the handle from the field of surgery to give the surgeon the ability to maneuver an instrument 15 about or along the top surface 22 and longitudinal axis L of the blunt blade 20.

The handle 60 has a first end 62 disposed adjacent the top end 54 of the separating member 50 and connected thereto by the connecting, or an attaching, means. As shown in FIG. 1, it is preferred that the handle 60 is rotatable about an axis of rotation R. To allow this rotation, the connecting means further comprises a means for selectively positioning the handle 60 at a selected one of a plurality of desired radial positions about the axis of rotation R.

As shown best in FIGS. 1 and 2, the selectively positioning means comprises a first member 70 having a lower surface 72 fixedly attached to the top surface 22 of the separating member 50 and a second member 80. The second member 80 has an exterior surface 82 and is rotatable relative to the first member 70 about the axis of rotation R. The first end 62 of the handle 60 is fixedly attached to a portion of the exterior surface 82 of the second member 80. A portion of the first and second members 70, 80 are of a complementary size with each other so that the first and second members 70, 80 may securably and detachably engage each other when the handle 60 and attached second member 80 are disposed at the desired radial position.

In the presently preferred embodiment, the first member 70 comprises at least one cleat 74 and the second member 80 comprises a disk member 84 defining a plurality of slots 86 therein. Each slot 86 is of a size to complementarily receive one cleat 74 therein. The slots 86 are disposed radially about the axis of rotation R so that at least one of the slots 86 engages one cleat 74 at each of the desired radial positions.

Referring to FIG. 2, there are two cleats 74 and two slots 86 in the disk member 84. When the handle 60 is in a first desired radial position, which is disposed rearwardly relative to the blunt blade 20 and parallel its longitudinal axis L as shown in FIG. 1, each of the two cleats 74 engages a respective slot 86 in the disk member 84. When the handle 60 is turned 180° to a second desired radial position, shown in phantom line as 60' in FIG. 2, each of the two cleats 74 again engage a respective slot in the disk member 84. In the first desired radial position, the handle 60 is disposed for pushing the blunt blade 20 and in the second desired radial position, the handle 60 is disposed for pulling. Those skilled in the art will appreciate that other radial positions may be preferred, such as rotating the handle 60 perpendicular, or ninety degrees (90°), from the two desired radial positions shown.

Other embodiments of the selectively positioning means are contemplated. Examples include the first and second members 70, 80 having complementary knurled surfaces or having complementary detents and interfacing protrusions. As those skilled in the art will appreciate, these alternate embodiments can be constructed to allow the handle 60 to be disposed at numerous desired radial positions.

The selectively positioning means can further comprise a means for rotatably aligning the second member 80 as it rotates relative to the first member 70. Referring to FIGS. 1 and 2, the second member 80 defines a passage 88 therethrough that extends along the axis of rotation R. In conjunction, the aligning means comprises a rod 90 that has an exterior surface 92. The rod 90 is of a size to be complementarily received into the passage 88 so that the second member 80 and attached handle 60 are rotatable about the rod 90.

Preferably, the selectively positioning means also comprises a means for locking the second member 80 at the selected desired radial position. The locking means preferably comprises a nut 94 that defines a duct 96 extending therethrough and that has one side 98 disposed adjacent a portion of the second member 80. The duct 96 is of a size to receive a portion of the rod 90 therein. The duct 96 and the exterior surface 92 of the rod 90 also have complementary threaded surfaces so that the nut 94 is movable along the rod 90 between a locking position and a release position. In the locking position, a portion of the nut 94 contacts a portion of the exterior surface 82 of the second member 80 so that the second member 80 engages the first member 70, even when an upward force is applied to the handle 60. In the release position, the nut 94 is spaced apart from the second member 80 so that the second member 80 can be separated from the first member 70 and rotated from one desired radial position to another desired radial position. In use, the surgeon twists the nut 94 loose so that the handle 60 can be rotated between the first and second desired radial positions and, when in the chosen desired radial position, the surgeon re-tightens the nut 94.

One embodiment of the invention provides a method of lysing a retrosternal adhesion resulting from a previous sternotomy at a predetermined site in a patient. "Retrosternal" means the area beneath, behind or adjacent the posterior or dorsal surface of the sternum, i.e., the surface or portion of the sternum facing the thoracic cavity. The patient can be any patient, but is preferably a human subject.

In general, the method comprises accessing the retrosternal area through a thoracotomy incision that is adjacent to the anterior (or ventral) midline of the patient near the caudal end of the patient's sternum S. The previous sternal incision is incised an the incision is taken down to the sternum S sharply or with electrocautery. The previous sternal incision is extended toward the umbilicus approximately two inches below the caudal end of the sternum S. The rectus facia is then opened in the mid-line to allow access to the retrosternal area.

A plane is developed behind or underneath the sternum S sharply under direct vision. The manubrium is removed if it is present. A rake or a retractor can then be placed at the caudal end of the sternum S and the caudal end of the sternum is elevated away from the heart H. This creates a slightly wider plane between the sternum and the heart.

The redo sternotomy retractor 10 provided by the present invention is then introduced into the plane behind the sternum S so that the space between the sternum S and underlying tissues can be clearly visualized adjacent the distal end 26 of the blade 20 by application of the appropriate downward pressure to the retractor 10. As shown in FIG. 2, a working space or tunnel is created between the top surface of the blunt blade 20 and the posterior or dorsal surface of the sternum S and along the longitudinal axis thereof. Underlying tissues are retracted away and protected by the blade 20 as lysis of adhesions is preformed by the surgeon.

In one embodiment, as shown in FIGS. 1–3, the retractor 10 can be adapted for endoscopic attachment. Once connected to an endoscope, retrosternal adhesions are clearly seen on the video screen, especially adhesions which occur near the cranial terminus of the sternum. It is also contemplated that an endoscope can be passaged in the tunnel created between the top surface 22 of the blade 20 and the posterior (or dorsal) surface of the sternum S along with other instruments.

Once the retractor 10 is properly positioned, the retrosternal adhesions can be lysed and divided (dissected away)

utilizing electrocautery coupled with suction, preferably under endoscopic control and visualization. As the adhesions are taken down, the retractor 10 is slowly advanced cephalad so that within several minutes the full extent of the retractor 10 is behind the sternum S.

Although the present invention has been described with reference to specific details of certain embodiments thereof, it is not intended that such details should be regarded as limitations upon the scope of the invention except as and to the extent that they are included in the accompanying claims.

What is claimed is:

1. A sternotomy retractor, comprising:
   a. a longitudinally-extending blunt blade having a longitudinal axis, a top surface, a bottom surface, a distal end, an opposed proximal end, and an edge circumscribing said blunt blade;
   b. a separating member having a bottom end fixedly attached to a portion of said blunt blade adjacent the proximal end thereof and an opposed top end, wherein said separating member is oriented to allow longitudinal movement of a surgical instrument along at least a portion of the top surface of said blunt blade unobstructed by said separating member, wherein said separating member is arcuate;
   c. a handle having a first end disposed adjacent the top end of said separating member; and
   d. means for connecting the first end of said handle to the top end of said separating member, wherein said blunt blade comprises a first section disposed adjacent the distal end of said blunt blade and an adjacent second section, the top surface of said first section and said second section being linear along the longitudinal axis of said blunt blade, said top surface intermediate said first and second sections being nonlinear along said longitudinal axis so that the top surfaces of said first and second sections are nonlinear with respect to each other, the top surface of said first section being disposed closer to the bottom surface of said first section than the top surface of said second section.

2. The sternotomy retractor of claim 1, wherein said separating member laterally spaces apart the first end of said handle from said blunt blade.

3. The sternotomy retractor of claim 2, wherein said separating member is disposed over the top surface of said blunt blade when said blunt blade is horizontally disposed.

4. The sternotomy retractor of claim 3, wherein said separating member comprises a "C" shaped member.

5. The sternotomy retractor of claim 1, wherein said separating member comprises a "C" shaped member.

6. A sternotomy retractor, comprising:
   a. a longitudinally-extending blunt blade having a longitudinal axis, a top surface, a bottom surface, a distal end, an opposed proximal end, and an edge circumscribing said blunt blade;
   b. a separating member having a bottom end fixedly attached to a portion of said blunt blade adjacent the proximal end thereof and an opposed top end, wherein said separating member is oriented to allow longitudinal movement of a surgical instrument along at least a portion of the top surface of said blunt blade unobstructed by said separating member, wherein said separating member is arcuate;
   c. a handle having a first end disposed adjacent the top end of said separating member; and
   d. means for connecting the first end of said handle to the top end of said separating member, wherein said handle is rotatable about an axis of rotation and wherein said connecting means further comprises means for selectively positioning said handle at a selected one of a plurality of desired radial positions about said axis of rotation.

7. The sternotomy retractor of claim 6, wherein said selectively positioning means comprises:
   a. a first member having a lower surface fixedly attached to the top surface of said separating member; and
   b. a second member having an exterior surface and being rotatable relative to said first member about the axis of rotation of said handle, the first end of said handle being fixedly attached to a portion of the exterior surface of said second member, wherein at least a portion of said first and second members are of a complementary size to each other so that said first and second members securably and detachably engage with each other when said second member is disposed at one desired radial position relative to said first member.

8. The sternotomy retractor of claim 7, wherein said first member comprises at least one cleat and wherein said second member comprises a disk member defining a plurality of slots therein, each of said slots being of a size to complementarily receive one cleat therein, said slots being disposed radially about the axis of rotation of said handle so that at least one of said slots engages one of said cleats at each of the desired radial positions.

9. The sternotomy retractor of claim 8, wherein said selectively positioning means further comprises means, disposed along the axis of rotation of said handle, for rotatably aligning said second member as said second member rotates relative to said first member.

10. The sternotomy retractor of claim 9, wherein said second member defines a passage therethrough, said passage extending along the axis of rotation of said handle, and
    wherein said aligning means comprises a rod having an exterior surface and being of a size to be complementarily received into said passage so that said second member is rotatable about said rod.

11. The sternotomy retractor of claim 10, wherein said selectively positioning means further comprises means for locking said second member at the selected desired radial position.

12. The sternotomy retractor of claim 11, wherein said locking means comprises a nut defining therethrough and having one side disposed adjacent a portion of said second member, said duct being of a size to receive a portion of said rod therein, said duct and the exterior surface of said rod having complementary threaded surfaces so that said nut is movable along said rod between a locking position, in which a portion of said nut contacts a portion of the exterior surface of said second member, and a release position, in which said nut is spaced apart from said second member so that said second member is rotatable from one desired radial position to another desired radial position.

13. A sternotomy retractor, comprising:
    a. a longitudinally-extending blunt blade having a longitudinal axis, a top surface, a bottom surface, a distal end, an opposed proximal end, and an edge circumscribing said blunt blade;
    b. a separating member having a bottom end fixedly attached to a portion of said blunt blade adjacent the proximal end thereof and an opposed top end, wherein said separating member is oriented to allow longitudinal movement of a surgical instrument along at least a portion of the top surface of said blunt blade unobstructed by said separating member, wherein said separating member is arcuate;

c. a handle having a first end disposed adjacent the top end of said separating member; and d. means for connecting the first end of said handle to the top end of said separating member; and e. a longitudinally-extending tube defining a bore therethrough and having a first end disposed adjacent the proximal end of said blunt blade, an opposed second end, and an outer surface, said bore extending substantially parallel to the longitudinal axis of said blunt blade and being of a size to allow a predetermined surgical instrument to be slidably received therein, at least a portion of said outer surface being fixedly attached to the top surface of said blunt blade.

14. The sternotomy retractor of claim 13, further comprising a bayonet endoscopic fitting fixedly attached to the first end of said tube, wherein said fitting may detachably secure a predetermined surgical instrument slidably received in said tube at a desired longitudinal position.

15. A retractor, comprising:

a. a longitudinally-extending blunt blade having a longitudinal axis, a top surface, a bottom surface, a distal end, an opposed proximal end, and an edge circumscribing said blunt blade;

b. a handle having a first end disposed adjacent the proximal end of said blunt blade; and c. means for attaching the first end of said handle to the proximal end of said blunt blade, said attaching means allowing longitudinal movement of a surgical instrument along at least a portion of the top surface of said blunt blade that is unobstructed by said attaching means and said handle, wherein said attaching means is arcuate, wherein said attaching means comprises a "C" shaped member having a body portion, said "C" shaped member having a bottom end fixedly attached to the proximal end of said blunt blade and an opposed top end, the first end of said handle being attached to said top end, wherein said handle is rotatable about an axis of rotation and wherein said attaching means further comprises means for selectively positioning said handle at a selected one of a plurality of desired radial positions about said axis of rotation.

16. The retractor of claim 15, wherein said "C" shaped member laterally spaces apart the first end of said handle from said blunt blade.

17. The retractor of claim 15, wherein at least a portion of the edge of said blunt blade adjacent the distal end thereof is arcuate.

18. A sternotomy retractor, comprising:

a. a longitudinally-extending blunt blade having a longitudinal axis, a top surface, a bottom surface, a distal end, an opposed proximal end, and an edge circumscribing said blunt blade, wherein said blunt blade comprises a first section disposed adjacent the distal end of said blunt blade and an adjacent second section, the top surface of said first section and said second section being linear along the longitudinal axis of said blunt blade, said top surface intermediate said first and second sections being nonlinear along said longitudinal axis so that the top surfaces of said first and second sections are nonlinear with respect to each other, the top surface of said first section being disposed closer to the bottom surface of said first section than the top surface of said second section; and b. a handle connected to a portion of said blunt blade adjacent the proximal end thereof.

* * * * *